United States Patent
Antonoplos et al.

(10) Patent No.: US 6,551,555 B2
(45) Date of Patent: *Apr. 22, 2003

(54) APPARATUS WITH A CHEMICAL INDICATOR FOR INDICATING EXPOSURE TO AN OXIDATIVE STERILANT OR DISINFECTANT

(75) Inventors: Patricia A. Antonoplos, Newport Beach, CA (US); Henry K. Hui, Laguna Niguel, CA (US); Alireza Ebrahim, Foothill Ranch, CA (US); Leslie A. Feldman, Calabasas Hills, CA (US); Nitu Kohli, Lake Forest, CA (US)

(73) Assignee: Ethicon, Inc., New Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/741,633

(22) Filed: Dec. 19, 2000

(65) Prior Publication Data

US 2002/0051733 A1 May 2, 2002

Related U.S. Application Data

(63) Continuation of application No. 09/290,592, filed on Apr. 13, 1999, now Pat. No. 6,218,189, which is a continuation of application No. 08/966,397, filed on Nov. 7, 1997, now Pat. No. 5,942,438.

(51) Int. Cl.[7] .................................................. G01N 31/12
(52) U.S. Cl. ............................ 422/58; 422/57; 422/61; 436/1; 436/166
(58) Field of Search .............................. 422/57, 58, 61, 422/28, 34, 37; 436/1, 2, 166

(56) References Cited

U.S. PATENT DOCUMENTS

| | | |
|---|---|---|
| 3,258,312 A | 6/1966 | Olson et al. |
| 3,263,892 A | 8/1966 | Danyi et al. |
| 3,627,469 A | 12/1971 | Cheng et al. |
| 3,667,916 A | 6/1972 | Sliva et al. |
| 3,704,096 A | 11/1972 | Verses et al. |
| 3,852,034 A | 12/1974 | Gunther |
| 3,948,727 A * | 4/1976 | Steiger ...................... 435/242 |
| 4,015,937 A | 4/1977 | Miyamoto et al. |
| 4,191,048 A | 3/1980 | Molina |
| 4,263,197 A | 4/1981 | Lienhard et al. |
| 4,298,569 A | 11/1981 | Read |
| 4,407,960 A | 10/1983 | Tratnyek |
| 4,521,376 A | 6/1985 | Wittonsky et al. |
| 4,521,506 A | 6/1985 | Stolzenburg et al. |
| 4,551,211 A | 11/1985 | Kobayashi et al. |
| 4,675,161 A | 6/1987 | Hashimoto et al. |
| 4,880,466 A | 11/1989 | Zwarun et al. |
| 5,057,434 A | 10/1991 | Prusik et al. |
| 5,110,492 A | 5/1992 | Casey |
| 5,270,344 A | 12/1993 | Herman |

(List continued on next page.)

FOREIGN PATENT DOCUMENTS

EP  421 760 A1  4/1991

*Primary Examiner*—Lyle A. Alexander
(74) *Attorney, Agent, or Firm*—Knobbe Martens Olson & Bear LLP

(57) ABSTRACT

An apparatus for determining exposure to an oxidative sterilant is described. The apparatus includes a chemical indicator for indicating exposure to the oxidative sterilant and a biological indicator for determining the effectiveness of the exposure to the oxidative sterilant. The chemical indicator has a metallic surface with a non-pH sensitive permanent indicator on the surface for indicating exposure to the oxidative sterilant. The chemical indicator may be on a self-contained biological indicator. The biological indicator and chemical indicator may be inside a test pack, where the test pack restricts sterilant flow to the indicators.

17 Claims, 2 Drawing Sheets

U.S. PATENT DOCUMENTS

| | | |
|---|---|---|
| RE34,515 E | 1/1994 | Foley |
| 5,358,962 A | 10/1994 | Oura et al. |
| 5,405,580 A | 4/1995 | Palmer |
| 5,418,167 A | 5/1995 | Matner et al. |
| 5,518,927 A | 5/1996 | Malchesky et al. |
| 5,524,755 A | 6/1996 | Deeds |
| 5,645,824 A | 7/1997 | Lim et al. |
| 5,679,442 A | 10/1997 | Haindl |
| 5,942,438 A | 8/1999 | Antonoplos et al. |
| 5,955,025 A | 9/1999 | Barrett |

* cited by examiner

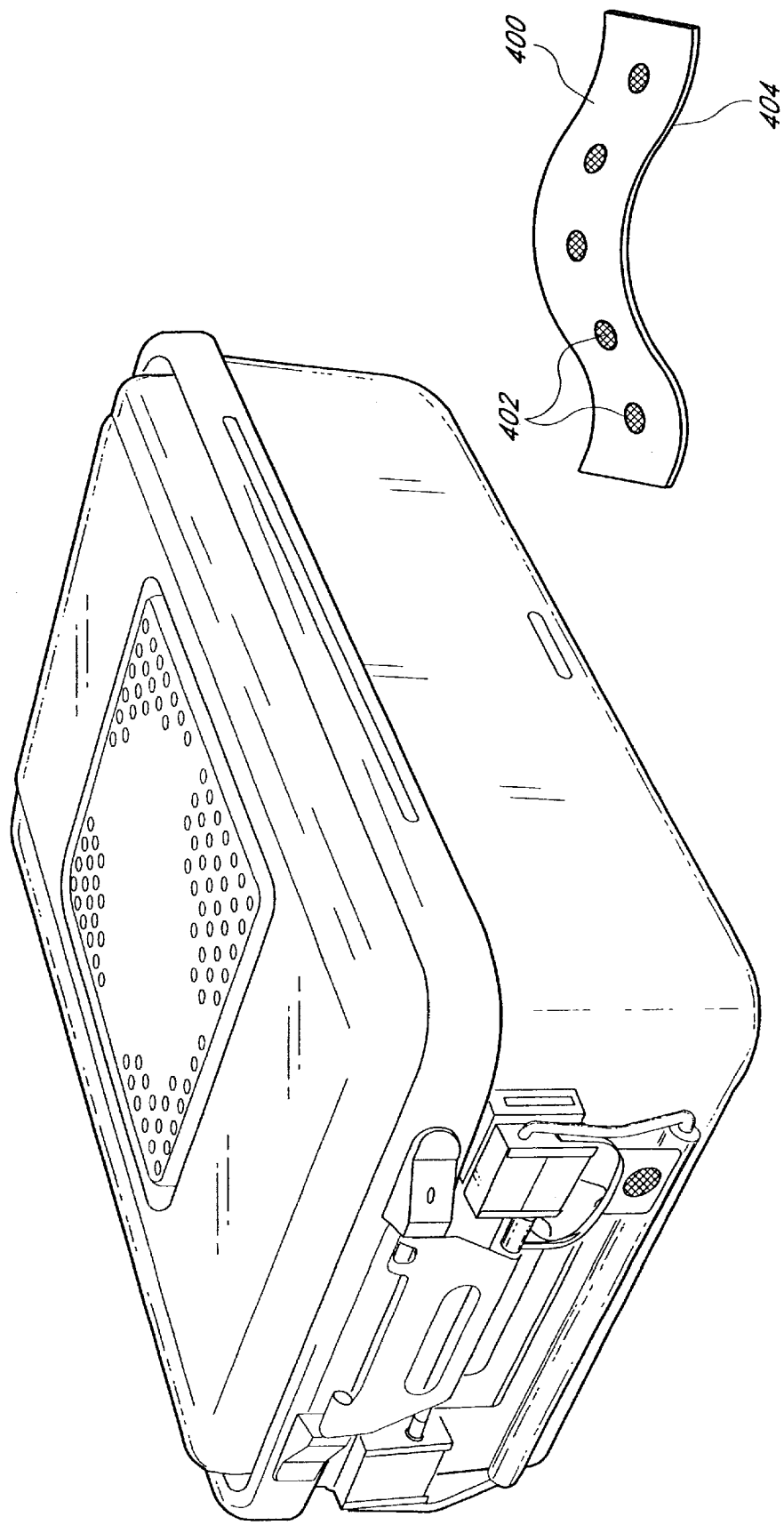

APPARATUS WITH A CHEMICAL INDICATOR FOR INDICATING EXPOSURE TO AN OXIDATIVE STERILANT OR DISINFECTANT

RELATED APPLICATIONS

The present application is a continuation of U.S. application Ser. No. 09/290,592, filed Apr. 13, 1999, now U.S. Pat. No. 6,218,189 which is a continuation of U.S. application Ser. No. 08/966,397, filed Nov. 7, 1997, now U.S. Pat. No. 5,942,438.

FIELD OF THE INVENTION

The invention relates to an apparatus including a chemical indicator for indicating exposure to an oxidative sterilant and a biological indicator for determining the effectiveness of exposure to the oxidative sterilant.

BACKGROUND OF THE INVENTION

A variety of medical instruments are used for the diagnosis and treatment of medical ailments. Transmission of microorganisms to a patient from a medical device can result in a serious disease or death. The medical instrument used to treat the medical ailment is preferably free of microorganisms which thereby minimizes the spread of disease or infection to the patient. A method of sterilizing medical instruments comprises providing an oxidative sterilant or disinfectant in the form of liquid, gas, or gas-plasma to a sealed chamber housing the medical instruments. One sealed chamber type device is the STERRAD® Sterilization System available through Advanced Sterilization Products of Irvine, Calif., a division of Johnson & Johnson Medical, Inc. Providing the sterilant in gas or plasma form (hereinafter "gas") is especially desirable because the gas renders the surface of the medical device sterile, thereby rendering viruses and bacteria harmless. Likewise, the gas spreads to enclosed or isolated areas of the medical instrument which would otherwise not be sterilized. After a period of time the sterilant in gas form render the devices sterile and a medical technician removes the medical instruments from the chamber.

The importance of achieving complete sterilization motivates placing an indicator in the chamber with the medical instruments to provide verification that an adequate amount of sterilant was provided to the chamber. The prior art method of verifying if the sterilant had entered the chamber comprised placing a chemical indicator and a biological indicator in the chamber. A chemical indicator comprises a surface having a chemical thereon which changes color upon exposure to a sterilization process. Chemical indicators are often integrated with other sterilization verification devices to provide additional evidence of exposure to sterilant. Biological indicators are packages which contain a high number of bacterial spores. The biological indicator, after being exposed to sterilant, is culture tested to determine if the bacteria are viable. If the sterilization was successful, the bacteria contained within the biological indicator will not grow.

In general, chemical indicators should satisfy several basic performance characteristics. The chemical indicator should be readable, reliable, selective, stable, and safe. These performance characteristic are explained in more detail in Volume 1 of the Sterilization Standards Committee of the Association for the Advancement of Medical Instrumentation (AAMI) and by the General Requirements for Chemical Indicators of the proposed American National Standard Institute (ANSI) drafted by Chemical Indicators Working Group. These two documents are incorporated herein by reference.

Chemical indicators of the prior art generally comprise a pH-sensitive material placed on a medium. Simply, the pH-sensitive chemical indicator changes color when exposed to an acidic oxidation-type sterilant, such as $H_2O_2$ or $H_3CCOOOH$, for a sufficient amount of time. The color change occurs from a chemically induced pH change, i.e., from basic to acid. For example, exposure to an acidic oxidation-type sterilant can change the color of a pH-sensitive chemical indicator from blue to yellow or colorless or from red to yellow. The pH-sensitive chemical indicators of the prior art can also be placed within containers known as test packs. A test pack is a structure which provides a challenge to the sterilization process and thereby provides a more realistic representation of actual conditions of certain areas on medical devices.

The pH-sensitive chemical indicators of the prior art suffer from several disadvantages and may not fully satisfy basic performance characteristics related to stability and selectivity. Since pH-sensitive chemical indicators are chemically reversible, their processed and unprocessed colors can change upon exposure to certain chemicals, especially those with acidic or basic characteristics. Poor pre-processing color stability of pH-sensitive chemical indicators of the prior art is undesirable because it requires chemical indicators to be discarded after a relatively short shelf life thereby wasting supplies. Furthermore, a chemical indicator of the prior art which is on the verge of changing color due to chemical instability does not provide an accurate chemical exposure indication when utilized in a sterilization chamber. Additionally, a short pre-processing shelf life for the chemical indicator is even more undesirable when the chemical indicator is integrated with a biological indicator because an even more expensive device (test pack, including chemical indicator and biological indicator) must be discarded when the pH-sensitive chemical indicator changes color.

Poor post-processing color stability of pH-sensitive chemical indicator of the prior art is also undesirable because the chemical indicator will return to its original color if exposed to a base and, thus, the processed chemical indicator cannot be used as a permanent record of the sterilization process. Therefore, if exposed to a base, the chemical indicator will revert to the original color and provide an unprocessed appearance. This characteristic of pH-sensitive chemical indicators of the prior art is particularly undesirable because using a chemical indicator more than once may provide a faulty processing indication. In a yet different scenario, the indicator could mislead a technician by providing an unprocessed reading when, in fact, the load was processed. This would lead to repeated sterilization cycles thereby increasing cost.

Finally, the pH-sensitive indicators of the prior art are not very selective and may change color upon exposure to any of a number of reagents, not just oxidation-type sterilants. Thus, an indicator may change color from exposure to an acidic reagent and not from adequate exposure to a sterilant. Such an inappropriate color change is misleading and could lead to misinterpretation of result.

Another type of chemical indicator is disclosed in U.S. Pat. No. 5,518,927 entitled "INSTRUMENT STERILIZATION [sic] LIFE-SPAN INDICATOR" to Malchesky et al. The Malchesky reference discloses using crystal violet pigment sandwiched between two plastic members and attaching the plastic tag formed therefrom to an instrument during a sterilization process. After repeated exposures, the pigment changes color. Based on the color of the pigment sandwiched between the layers of plastic, the number of sterilizations, i.e. uses, which the instrument has undergone may be determined.

The Malchesky reference discloses a chemical indicator which suffers from numerous disadvantages and drawbacks. First, crystal violet dye possess pH-sensitivity at the extreme lower end of the pH scale. In fact, according to the Handbook of Stains, Dyes, and Indicators by Floyd J. Green, the visual-transition interval is pH 0.0 (yellow) to pH 2.0 (blue-violet) using a 0.02% aqueous solution of crystal violet. Thus, since crystal violet dye is pH-sensitive, chemical indicators which utilize crystal violet suffer from the same drawbacks as pH-sensitive chemical indicators of the prior art.

In response to these drawbacks, the Malchesky reference teaches enclosing the crystal violet dye in a plastic covering or tag to prevent the acidic sterilant from contacting the pH-sensitive crystal violet dye. However, enclosing the dye in plastic creates further disadvantages. The first disadvantage is that the plastic tag is prone to simply falling off. Alternatively many medical instruments do not provide a place to attach a tag, or if such a place it provided, the tag may severely interfere with the operation and performance of the medical device.

The Malchesky reference also teaches using crystal violet or other organic dyes. However, crystal violet, and many organic dyes in general, are toxic if released from their plastic cover. For example, crystal violet, which has catalog number 229288 in the Sigma-Aldrich Chemical Company database, is a cationic triarylmethane dye, is toxic and may cause cancer, heritable genetic damage and irritate the eyes, respiratory system and skin. Thus, the invention of the Malchesky reference suffers from another serious drawback.

Therefore, a need exists for a chemical indicator for use with oxidation-type sterilization systems which does not chemically break down, has increased sensitivity and will not give false indications upon exposure to common chemical compounds and conforms with the performance characteristic of the AAMI Sterilization Standards Committee. The present invention satisfies that need.

SUMMARY OF THE INVENTION

One aspect of the invention involves an apparatus for determining exposure to an oxidation-type sterilant or disinfectant. The apparatus contains a biological indicator for determining the effectiveness of exposure to the oxidation-type sterilant and a chemical indicator for indicating exposure to the oxidation-type sterilant. The chemical indicator includes a metallic surface and a non-pH sensitive indicator on the surface for indicating exposure to the oxidation-type sterilant.

Advantageously, the indicator is an azo dye. Preferably, the indicator is a permanent indicator. In an embodiment, the surface is anodized aluminum. Preferably, the surface includes a chromate conversion coating. Advantageously, the biological indicator is a self-contained biological indicator. In an embodiment, the chemical indicator includes a generally flat disk on the self-contained biological indicator. The apparatus may also include a test pack, where the test pack is configured to provide for gas flow into the test pack by diffusion and where the chemical indicator and the biological indicator are inside said test pack. Advantageously, the apparatus includes a container having a cover, where the cover is secured to the container with a tamper-evident device, where the surface with the non-pH sensitive bleachable dye is on the tamper-evident device.

In an embodiment, the metallic surface includes a flexible medium having the indicator on the surface of the flexible medium. Preferably, the apparatus includes adhesive on the opposite side of the flexible medium than the indicator. The apparatus may also include a warranty indicator which provides notice when the warranty of the apparatus is still in effect. Advantageously, the oxidation-type sterilant includes hydrogen peroxide. Preferably, the hydrogen peroxide is aqueous hydrogen peroxide. Advantageously, the hydrogen peroxide is hydrogen peroxide vapor or gas.

BRIEF DESCRIPTION OF THE DRAWINGS

FIG. 3 illustrates a container having a tamper-evident device incorporating a chemical indicator comprised of bleachable dye.

FIG. 4 illustrates a flexible medium or tape incorporating a chemical indicator comprised of bleachable dye.

DETAILED DESCRIPTION OF THE PREFERRED EMBODIMENT

Figure 1:
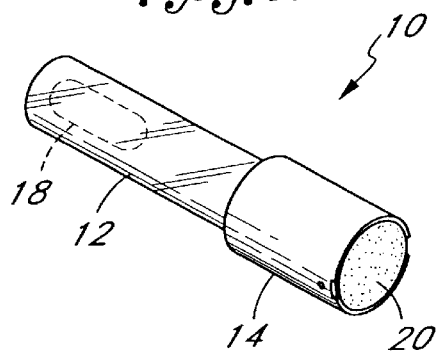
FIG. 1 illustrates a form of a self-contained biological indicator having a chemical indicator portion comprising bleachable dye.

The present invention comprises a chemical indicator for oxidation-type sterilization processes. This invention provides a new type of chemical indicator comprising a bleachable dye which permanently changes color upon exposure to an oxidizing or bleaching sterilant. Advantageously, the present invention does not suffer from the drawbacks of the prior art. First, the dye on the chemical indicator is chemically and environmentally stable thereby increasing shelf life. Second, the dye is generally not pH-sensitive and hence will not undergo color change if accidentally exposed to a base or acid. Third, the claimed chemical indicator is more versatile than chemical indicators of the prior art, because it can be manufactured to change color after a single exposure to sterilant or after multiple exposures to sterilant. Likewise, this new chemical indicator is selective to certain oxidation-type sterilants and does not change color upon exposure to steam, water, light or other acidic or basic compounds. Furthermore, the permanent color change prevents the chemical indicator from reversing color after a sterilization process. Finally, cytotoxicity test results indicate that the processed and unprocessed chemical indicators claimed herein are noncytotoxic and pose no safety risk to the users.

The bleachable dye is a chemical composition comprising a non-pH-sensitive dye which upon exposure to an oxidation-type sterilant changes color due to oxidation. Preferably, the dye comprises an azo dye. More preferably the dye comprises a metallic azo dye integrated on a metallic surface through an anodization or chromate conversion process. Many different types of metallic azo dyes exist, including, but not limited to the following:

Aluminum Bordeaux R
Aluminum Bordeaux RL
Aluminum Fiery Red ML
Aluminum Orange 3A
Aluminum Yellow 4A
Aluminum Yellow G3LW Aluminum Green LWN
Aluminum Violet CLW
Aluminum Brown BL
Aluminum Olive Brown 2R
Aluminum Grey BL
Aluminum Black BK
Aluminum Gold S The above list of dye is not exhaustive and is provided by way of example. Other azo dyes likely exist and are covered by the scope of the present application. Likewise, although the preferred embodiment is realized utilizing metallic azo dyes, it is contemplated that other types of bleachable dyes could be used interchangeably. In the preferred embodiment described herein the substrate comprises aluminum, or an alloy thereof. However, it is contemplated that other metallic base materials, such as stainless steel, titanium, and other alloys can be utilized for substrate material. Likewise, it is also contemplated that other, nonmetallic materials may serve as substrate material. These materials include plastic, paper, cellulose-based fabric, and fiberglass.

The oxidation-type sterilants are of the type commonly used in sterilization system, such as the STERRAD® Sterilization System made by Advanced Sterilization Products of Irvine, Calif. The sterilants which are contemplated for use with the chemical indicators claimed herein include, but are not limited to, chlorine dioxide, ozone, hydrogen peroxide, and peracetic acid. Other sterilants which effect a color change in the dyes described herein are also operable with the present invention.

The process of manufacture, described in more detail below, comprises placing the dye on or integrating with the anodization or chromate conversion coated surface on an aluminum substrate. The surface acts as a carrier for the dye and is preferably semi-permeable thereby providing for the dye and sterilant to penetrate the surface or structure. Advantageously, integration of the dye with the metallic surface prevents the dye from rinsing or washing out of the chemical indicator.

In addition to the application for a single cycle process indicator, this manufacturing capability makes the dye also suitable for use as a limited re-use indicator or as a warranty expiration indicator.

Five primary factors control the number of exposures or amount of exposure time required to change the color of the dye. The first factor is the amount of time that the dye is exposed to the surface. The second factor is the porosity and thickness of the layer on which the dye is placed. The third factor is the oxidation resistance of the dye. The fourth factor is the degree to which the surface is sealed using sealant. The fifth factor is the concentration of oxidant and exposure time to which the dye is exposed. Other factors beyond those enumerated also effect the rate of color change, although not as significantly as the five enumerated above. The five factors are discussed in more detail below. The process for applying the bleachable dye to a surface depends upon the surface to which the dye is applied and the intended use of the indicator created therefrom.

One material that is often used to construct medical instruments is aluminum alloy with either an anodized coating or a chromate conversion coating. One form of aluminum alloy which may be used is 5052-H32 although other types of material are covered by the inventive scope of the present invention. The anodized aluminum or chromate conversion layer creates a particularly desirable surface in which to impregnate the dye because both coatings have a porous surface layer which absorbs the dye. The dye becomes stable in the upper surface of either layer thereby securing the dye during standard washing or handling yet allows the gaseous oxidizing sterilants to penetrate the porous surface to thereby bleach or oxidize the dye to a different color.

Method of Manufacture

A six step process is utilized to form the chromate conversion coated aluminum. The six steps are cleaning, coating, rinsing, dyeing, rinsing and drying. Cleaning removes any oils that remain on the aluminum after machining and/or fabrication, de-oxidizes the surface and removes any light oxide film to thereby ensure that the dye absorbs evenly. Cleaning is performed by a series of acidic, basic, and de-oxidizing rinses. The steps and the details described herein first comprise washing the aluminum. Washing comprises exposing the aluminum to inhibited nonetching alkaline soap at a concentration of 5–6 ounces per gallon at 140–150° Fahrenheit (F.) and upon completion rinsed with water. Next, the surface is rinsed with nitric acid having a concentration of 20–25% by volume at a temperature of 140–150° F. The surface is rinsed with water before being etched with caustic soda at a concentration of 5.5–6.0 ounces per gallon and a temperature of 145–150° F. The surface is rinsed again to remove any excess caustic soda. Finally, the surface is exposed to a de-oxidizer to remove any unwanted oxidation. The de-oxidizer is at a concentration of 16 ounces per gallon.

The second step comprises chromate coating. The chromate coat step comprises exposing the surface to Iridite 14–2 by dipping for 90 to 180 seconds thereby forming a chromate conversion coat on the surface of the aluminum alloy. The Iridite 14–2 is at a concentration of 12 grams per liter at a temperature of 70–95° F. Witco Chemical Corporation at Melrose Park, Ill. provides Iridite 14–2 and instructions for its use.

The third step comprises rinsing the chromate conversion coated aluminum with cold running water. This removes any impurities from the surface prior to dyeing.

Fourth, the coated aluminum is immersed in an aqueous dye solution containing Bordeaux Red, which has the trade name Aluminum Bordeaux RL powder, for 180 to 240 seconds at a temperature of 130–135° F. The dye has a pH of 3.0–3.5 and is mixed at a concentration of 16 grams per liter. The dye is provided by Clariant Corporation located in Charlotte, N.C. Dyes of various colors may be used, however, the color red, which bleaches to a yellow/gold color, advantageously maintains color uniformity with chemical indicators of the prior art. Advantageously other types and colors of dye are compatible with the apparatus and method described herein. Alternative methods of applying the dye also exist and including, but are not limited to, spraying, a moving liquid bath, brushing, or dipping.

The fifth step comprises rinsing the surface with cold running water. This step removes any excess dye and permanently sets the dye that is absorbed by the surface of the coated aluminum alloy. Of course, other methods of rinsing are available, such as agitation, spraying, spinning, or dipping in standing or running water.

Finally, the surface of the colored aluminum is air dried. As known by those of ordinary skill in the art, other methods of drying exist and are acceptable for use in the process described herein.

Also known by those of ordinary skill in the art is that the parameters of the above described process may be altered while still creating a surface having bleachable dye thereon which changes color upon exposure to an oxidation-type sterilant.

Sealed Anodized Aluminum

Another method and configuration of integrating a bleachable dye to a surface comprises dyeing and sealing anodized aluminum. This method and apparatus may provide another composition of bleachable dye indicator besides the chromate conversion coated aluminum described above.

The process for fabricating anodized aluminum containing a dye comprises first anodizing the aluminum surface on a medical instrument to form an oxide film. Next, the surface is immersed in a dye bath which causes the oxide film to absorb the dye to become colored. The final step is to seal the surface in a bath of hot water or solution of sealing salts. The process for preparing dyed anodized aluminum is known by those of ordinary skill in the art and is shown in U.S. Pat. No. 5,658,529 issued to Feldman and Hui, which is hereby incorporated by reference in its entirety herein.

Furthermore, the azo dye surface combination of the present invention made according to the above method of manufacture provides a permanent, nonreversible chemical indication. This overcomes the disadvantage of pH indicators which reverse color upon exposure to a base reagent. For example, crystal violet is pH-sensitive, i.e. changes color, when exposed to reagents having a pH of 0 to 2.5. Alternatively, the azo dyes of the present invention are generally not pH-sensitive and have resistance to color change even when exposed to reagents having a pH of 1 to 14.

Controlling the Rate of Color Change

As discussed briefly above, there are a number of ways to control the rate of color change, which is to say the number of exposures to a standard sterilization process before the dye changes color. The rate at which the dye changes color depends on the concentration of the bleaching agent to which the dye is exposed, the amount of time the dye is exposed to the surface, and the characteristics of the dye and the surface. When the concentration of the oxidation-type sterilant and the duration of the sterilizing process are known and fixed, such as in a sterilization chamber, the rate of change of the dye can be adjusted by controlling the factors listed above. When these controlling factors are also held constant, the rate of change for a particular sterilization procedure is known. Accordingly, a surface containing dye can be manufactured to change color after a predetermined number of sterilizations. This characteristic is especially desirable for use as an indicator for limited re-use devices or as a warranty expiration indicator, both of which are described below.

The factors which may be controlled during the processing stage in the production of a surface having bleachable dye thereon are the dye color, dye concentration, thickness, and porosity of the anodized or chromate conversion layer, alloy composition, anodization bath characteristics and sealant. A brief explanation for each of these factors follows.

Color of the Dye

Different dyes change color at different rates. Thus, by selecting a dye having a different color the number of sterilizations which must be undergone before the dye will change color can be controlled. This advantageously also provides a visual indication of the service life of an instrument, i.e., a color coded chart could be used to determine service life such that the color red indicates a service life of 10 uses, the color blue indicates a service life of three uses, etc. Advantageously, the bleachable dyes described herein are available in a wide range of colors including black, red, blue, green, yellow, gray and brown.

Concentration of the Dye

Likewise, the concentration of the dye will alter the degree of bleaching that occurs when the dye is exposed to an oxidation-type sterilant. Use of a high concentration dye mixture decreases the rate of color change. Applying dye in a low dye concentration mixture increases the rate of color change. Similarly, the length of time the dye is exposed to the surface will affect the amount of dye absorbed by the surface and accordingly will effect the rate of color change of the surface. If the dye is exposed to the surface for a long period of time then the surface will absorb more dye and color of the surface will change at a slower rate when exposed to an oxidizer.

Composition of the Surface Layer

The composition of the alloy will also affect the bleaching process. One of the primary reason for the difference in the rate of color change between different alloys is based on the porosity of the material, i.e. the material's ability to absorb the dye and the ability of the bleaching agent to penetrate the material during sterilization. Compositions of matter which are acceptable include, but are not limited to, anodized aluminum, chromate conversion layers or other such porus surfaces. It is also contemplated that other surface layers are compatible with the invention described herein.

Thickness of the Surface Layer

Controlling the thickness of the anodized or chromate conversion layer (hereinafter "layer") also controls the rate of color change. A thick surface layer will maintain the original color for a longer period of time then a thin layer. This occurs because a thick surface layer contains more dye than a thin surface layer and consequently the sterilant takes more time to penetrate the surface to reach the dye. Similarly, the application of the layer will also effect the behavior of the layer. For example, changing the chemical composition of the anodization or chromate conversion bath and/or the amount of electrical current used during the anodization process will affect the structure of the layer, which in turn effects the rate of color change of the dye. Anodizing aluminum and applying a chromate conversion layer are known by those of ordinary skill in the art, and accordingly not described in great detail herein.

Utilization of a Surface Sealant

Finally, placing a sealant over the surface will decrease the rate of color change of the dye contained thereunder. Accordingly, varying the amount and type of sealant will affect the characteristics of the dye. Various types of sealants exist and include but are not limited to water (hydration) or nickel compounds. Preferably, Anoseal 1000 type sealant from Noamax Technologies in Atlanta, Ga. is used as the sealant to control the rate of bleaching.

In Operation

To use a chemical indicator comprised of bleachable dye, the bleachable dye is preferably placed on a surface that is placed inside an oxidation-type sterilization chamber. The type of surface on which the chemical indicator is placed depends on the intended purpose or type of device with which the chemical indicator integrates.

The chemical indicator comprises a material having a section of bleachable dye thereon. The bleachable dye, as described, may be incorporated with a number of different devices, such as a stand alone chemical strip, a self-contained biological indicator incorporating a chemical indicator, a challenge pack, a test pack, tape or stickers, pouches, a limited re-use monitor, a warranty indicator, a tamper-evident device, and a documentation record (instrument count sheet).

The embodiments of the chemical indicators described herein provides for the chemical indicator to be placed inside a sterilization chamber with the medical devices that are being sterilized. The chemical indicator, having bleachable dye thereon, is also placed within the sterilization chamber. The chamber is sealed and the cavity within filled with a gaseous oxidation type sterilant. The sterilant remains sealed within the chamber for a time sufficient for the gaseous sterilant to render microorganisms harmless. The sterilant within the chamber contacts the dyed surface of the chemical indicator. While in contact, an oxidation process occurs thereby changing the color of the dyed surface to indicate exposure to the sterilant.

After an adequate sterilization period, the sterilant is evacuated from the chamber and the chemical indicator is examined. If the indicator has changed color, sterilant has been introduced into the chamber. To determine that the bacteria were inactivated, a biological indicator may also be placed within the chamber during the sterilization process, and later tested, using a culture, for potentially viable bacterial spores. Conversely, if the chemical indicator has not changed color, it can be inferred that the chemical indicator was not exposed to sterilant.

The process just described is applicable for single use chemical indicators such as chemical indicator strips, a self-contained biological indicator incorporating a chemical indicator, a challenge pack, a test pack, tape or stickers, pouches, tamper-evident devices, and documentation records (instrument count sheets), as well as limited re-use indicators and warranty indicators.

Response of Indicator to Partial Cycle Conditions

A chemical indicator having bleachable dye in an embodiment of a test strip was exposed to an oxidation-type sterilant and monitored for color response. The exposure time for the bleachable dye chemical indicator was reduced from the standard 50 minutes to 25 minutes thereby providing a difficult test for the chemical indicator.

25 Minute Test

A test was performed in a STERRAD® 100 Sterilizer using a partial cycle time of 25 minute diffusion and 15 minute plasma, at a concentration of 6 mg of hydrogen peroxide per liter using a simulated heavy load. Reducing the diffusion time from the standard 50 minutes to 25 minutes provides less time for the sterilant to reach the chemical indicator and less time for the sterilant to bleach the dye. Thus, this test provides a rigorous test of the bleachable dye chemical indicator.

As is known by those of ordinary skill in the art, various materials absorb more sterilant than other items. By way of example, polyurethane absorbs more sterilant than latex. The more sterilant that the medical instruments absorb, the less sterilant is available to reach the other areas of the chamber. Thus, test conditions mimicking a heavy load are configured to simulate actual conditions such as when the chamber is full of medical instruments that are partly comprised of materials which absorb the sterilant.

Four test pack configurations were used to test the chemical indicator of the present invention. The first test configuration was a stand alone configuration comprising a chemical indicator strip without any diffusion barriers. The second test configuration was a double pouched test configuration comprising a chemical indicator strip in a commercially available Mylar-Tyvek sterilization pouch. The third test configuration, illustrated in FIG. 2, was a biological indicator test pack (BITP) with a latex sample. The fourth test configuration was a BITP with a polyurethane sample. Polyurethane absorbs a large amount of sterilant thus making the fourth test configuration the most challenging.

Upon exposing the test configurations described above to the parameters of the test, each of the bleachable dye chemical indicators successfully changed from the color red to a yellow/gold color after a single process within the sterilization chamber thereby indicating adequate sterilant exposure.

Other Tests

The chemical indicators described herein underwent other testing. The testing was performed on a chromate conversion coated aluminum 5052 alloy chemical indicator made in accordance with the above described process. The tests reveal distinct advantages over the chemical indicators of the prior art.

Toxicity Tests

Toxicity tests on processed and unprocessed chromate conversion coated aluminum alloy base chemical indicator containing metallic azo dye were performed in accord with an in vitro biocompatibility study, based on the International Organization for Standardization (ISO 10993-5) guidelines to determine the potential for cytotoxicity from bleachables extracted from the material. The test extracts showed no evidence of causing cell lysis or toxicity. Thus, a further advantage of the chemical indicator of the present invention over the prior art is the complete lack of toxicity of the dye once impregnated or contained within the surface of the indicator.

Thus, another advantage of the metallic azo dye, metallic surface combination is the stability and lightfastness of the dye in the surface of the metal. Certain chemical indicator substances of the prior art were prone to washing out or to leaching from the surface of the chemical indicator. This can undesirably result in inaccurate readings and possible contamination of the medical devices. Since the dye as described herein is permanently bonded with the anodization or chromate conversion layer, the dye contained therein does not wash or rinse out.

Temperature/Humidity Resistance

Preliminary stability data for the aluminum chemical indicator show that the chemical indicator maintains its original color for at least three months when stored at 23° C. at 50% relative humidity, at 30° C. at 50% relative humidity, at 40° C. at 75% relative humidity, or at 50° C. with no relative humidity control. Based on the stability data at 50° C. and the fact that the rate of chemical reactions generally double for every 10° C. increase in temperature, it can be predicted that the aluminum chemical indicator will maintain its original color for at least 12 months if stored at 30° C. The present invention's stability is a distinct advantage over the prior art.

Photo Resistance

When exposed to a 30 watt fluorescence light at a distance of less than two feet at ambient conditions an unprocessed chemical indicator, as described above, maintained its original color for at least two months during an ongoing test. Furthermore, the aluminum chemical indicator maintained its processed color when exposed to a 30 watt fluorescence light at a distance of less then two feet at ambient conditions.

Acid and Base Resistance

As shown in Table 1 below, aluminum chemical indicators maintain their color when exposed to vapors from strong acids and strong bases at ambient conditions. Chemical indicators of the prior art which use Crystal Violet dye undesirably show a reversal in color under the same conditions.

TABLE 1

| Test Conditions | Prior Art Chemical Indicator | Aluminum Chemical Indicator |
| --- | --- | --- |
| Unprocessed CI exposed to Strong Acid | Color Change | No Change |
| Unprocessed CI exposed to Strong Base | Color Change | No Change |

Furthermore, the Aluminum Bordeaux RL dye of the embodiment disclosed herein maintains its color (red) in an aqueous solution having pH values of 1 to 14.

Steam Sterilization

A chemical indicator was exposed to a steam sterilization process in one test and exposed to an injection of water into the STERRAD Sterilization System in another test. The chemical indicator of the present invention did not change color. Thus, steam and water does not cause the color of the chemical indicator to change. This is a further advantage over the prior art which would often provide a false reading, i.e. change color, when exposed to steam or water.

Based on the testing detailed above, the claimed invention satisfies the reliability, selectivity, and stability requirements recommended by the Association of Advancement of Medical Instrumentation.

Alternative Embodiments

Several embodiments of the claimed invention are contemplated and described below. These are listed by way of example only, as the invention claim herein is intended to cover all applications incorporating the oxidation-type sterilant sensitive dyes.

Chemical Indicator Strip

In one preferred embodiment, a chemical indicator is formed using bleachable dye by placing the bleachable dye on a strip of material to form a chemical indicator strip. Indicator strips comprise generally small pieces of material having a chemical indicator section thereon. The chemical indicator strip is placed in a sterilization chamber and thereby exposed to an oxidation-type sterilant. Upon exposure for sufficient time to the sterilant, the chemical indicator portion of the strip changes color.

Chemical indicator strips are made in a way which is standard for applying dye to a strip of material. The bleachable dye may be sprayed, pressed, silk-screened, embedded, or brushed onto the strip. One of ordinary skill in the art is aware of the method of applying dye to a material, such as paper, plastic or metallic surface so the process is not described in detail herein. The chemical indicators may be placed in a sterilization chamber alone or as part of test pack or challenge pack, described below.

Self-Contained Biological Indicator

The chemical indicator of the claimed invention may also be integrated with a self-contained contained biological indicator. Self-contained biological indicators are described in detail in U.S. Pat. No. 5,405,580 to Palmer entitled Self-Contained Biological Indicators which is incorporated by reference in its entirety herein. FIG. 1 illustrates a self-contained biological indicator (SCBI) 10 integrating a chemical indicator having bleachable dye. The SCBI 10 comprises a semi-rigid container portion 12 and a cap section 14. Inside the container portion 12 are bacterial spores 18. Upon successful exposure to a sterilant the bacterial spores should be inactivated and may be tested to determine if the sterilization process was successful. However, determining if the bacterial spores are no longer viable requires that a culture be grown. To reduce the number of cultures which must be grown, a chemical indicator is incorporated with the SCBI thereby providing an inexpensive indication that the biological matter was exposed to a sterilant. If the chemical indicator does not indicate exposure to sterilant, then the bacteria within the biological indicator was not adequately exposed to sterilant and the time and expense of growing a culture may be avoided.

The cap section 14 contains a surface 20 containing bleachable dye. The indicator surface 20 may comprise a circular section on the top of the cap 14, as shown, or alternatively, the entire cap 14 or any section of the cap 14 or container portion 12, may be comprised of a material having bleachable dye thereon.

Alternatively, the container portion 12 may further house a glass vial containing a growth medium which, when broken by squeezing or pinching on the outer wall of the container portion 12, places the growth medium in contact with the bacterial spores 18. The growth medium indicates by color change the presence of viable spores.

In use, the one or more self-contained indicators 10 are placed in a sterilization chamber or other similar device, the chamber sealed and filled with gaseous sterilant. If the sterilant successfully enters the chamber for a sufficient period of time the chemical indicator having bleachable dye will change color. If the bleachable dye changes color then the biological material 18 may be used to grow a test culture. However, if the chemical indicator did not change color then the culture need not be grown.

Challenge Pack/Test Pack

Figure 2:
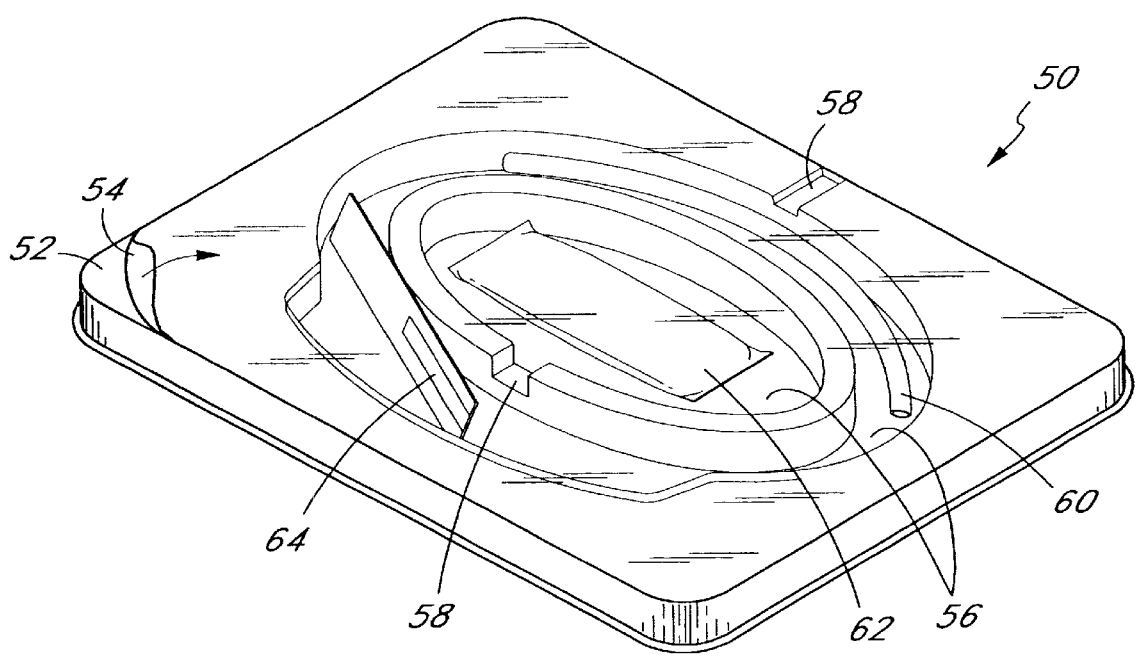
FIG. 2 illustrates a test pack incorporating a chemical indicator comprised of bleachable dye.

In another embodiment, the chemical indicator is incorporated with a challenge pack or a test pack. A test pack is used for the routine monitoring of the sterilization process, and simulates a "worst case" load. A challenge pack is intended to create a somewhat greater challenge to the sterilization process than the test pack or the load itself, and is used to validate a sterilizer upon installation or at regular intervals. Both a challenge pack and a test pack may contain a biological indicator and/or chemical indicator and have a structure which limits the movement of the gas accessing the indicators to movement by diffusion. FIG. 2 illustrates one preferred embodiment of a test pack 50. The test pack 50 has a base 52 formed with one or more inner depressions 56 with each depression gaseously connected by channels 58 to the other depressions and the volume outside the test pack.

A cover 54 rests on top of the base. The cover 54 has adhesive on some areas of its lower surface to secure and seal the cover to the base 52. Preferably the cover 54 is transparent thereby allowing items contained within the depressions 56 to be seen.

Located inside the test pack 50 is a piece of material, known as a sterilant absorber 60, a biological indicator package 62, and a chemical indicator strip 64. The sterilant absorber, usually polyurethane tubing or latex tubing, helps simulate actual test conditions by absorbing some of the oxidant. The biological indicator package 62 contains bacteria which may be in the form of spores. The chemical indicator strip 64 contains a section having bleachable dye.

In operation, the test pack 50 is exposed to an oxidation-type sterilant. Through diffusion the gaseous sterilizer enters the test pack through the channels 58 and thereby encounters the sterilant absorber 60. The sterilant absorber 60 absorbs some of the sterilant while the remaining sterilant flows to the other volumes of the depressions 56 of the test pack base 52. Eventually the gas comes in contact with the chemical indicator strip 64 and the biological indicator package 62.

Upon completion of the sterilization process, the test pack 50 is removed from the sterilization chamber and the chemical indicator strip 64 inspected for color change. If the chemical indicator strip 64 has changed color, i.e. the bleachable dye thereon has been bleached by the oxidation-type sterilant, then the sterilant has reached the inner volumes of the test pack for a sufficient amount of time and in sufficient concentration to warrant examination of the biological indicator package 62. Conversely, if the chemical indicator has not changed color then the sterilization process is not complete and should be repeated.

Tape and Other Tamper-Evident Devices

In another embodiment, the bleachable dye is incorporated into a tamper-evident device for sterilization containers. FIG. 3 illustrates a sterilization container. The sterilization container comprises a base 300 and a lid 304 having a number of openings 302 with filters (not shown) which allow sterilant to enter the sterilization container while preventing contaminants from entering. The base 300 and the lid 304 are configured to fit together to thereby form a seal between the base and the lid. Connected to the lid 304 is a clasp 310 which is configured to engage rods 314. Each rod 314 extends from a latch 316 on the base 300. Opening the latch 316 moves the rod 314 which in turn releases the clasp 310 to thereby facilitate removal of the lid 304.

A tamper-evident device 306 is used to provide evidence that the container has not been opened since sterilization. The tamper-evident device 306 possesses a pin 312 which is placed through the latch 316. The pin 312 secures to the opposite end of the tamper-evident device such that when the pin is secured it may only be removed by breaking the pin. When the pin 312 of the tamper-evident device 306 is in the latch 316 the latch can not be opened and consequently the lid can not be removed. Thus, the tamper-evident device and in particular the pin 312 must be removed from the latch 316 before the latch will open. The tamper-evident device 306 also contains a chemical indicator 308 comprising a non-pH-sensitive bleachable dye to indicate exposure to an oxidation type sterilant or disinfectant.

In operation, the base 300 contains medical devices in need of sterilization. The lid 304 is placed over the base 300 so that the clasp 310, rods 314, and latch 316 may be engaged to thereby secure the lid to the base. Next, the pin 312 of the tamper-evident device 306 is placed in the latch 316 and secured to the opposite end of the tamper-evident device. The container and medical devices within are placed within an sterilization chamber and exposed to sterilant for a sterilization cycle. During the sterilization cycle, the sterilant enters the container through the openings 302. When the container exits the sterilization chamber, the chemical indicator portion 308 of the tamper-evident device 306 is inspected to determine if the chemical indicator was exposed to sterilant. If exposed to sterilant the chemical indicator 308 changes color. The pin 312 of the tamper-evident device 306 remains within the latch 316 until the time of use for the medical instruments. Advantageously, the chemical indicator 308 on the tamper-evident device 306 indicates whether the sealed sterilization container has been exposed to sterilant, and if not broken, the tamper-evident device indicates that the container has not been opened, i.e. not exposed to outside contaminants. Furthermore, the non-pH-sensitive chemical indicator will not change color if exposed to an acid or base which would cause a false reading.

In yet another embodiment and as illustrated in FIG. 4, bleachable dye 402 resides on tape or a similar flexible medium 400 having adhesive 404 on one side. The flexible medium 400 may comprise, but is not limited to tape, stickers, or labels. On the side opposite the adhesive 404 is bleachable dye 402. The bleachable dye 402 may be sprayed, screen printed, rolled, or embedded, into or onto the tape or flexible medium 400. Advantageously, the dye 402 may be placed on the tape in the form of letters to provided directions for the operation of the dye or a color key to remind of the operation of the dye. An indicator tape which uses pH-sensitive dye which is presently available is STERRAD® Chemical Indicator Tape available through Advanced Sterilization Products located in Irvine, Calif. The Instructions for Use for the STERRAD® Chemical Indicator Tape are hereby incorporated by reference in their entirety herein.

In operation, the medical instrument is wrapped using a folding pattern, although other wrapping techniques are available, in a protective wrap or fabric. One such wrap is known by those of ordinary skill in the art as nonwoven sterilization wrap or, in particular, Kimberly Clark Spunguard which allows the sterilant to pass while preventing airborne contaminants such as dust and bacterial from depositing on the medical instrument wrapped therein. Once the medical instrument is wrapped within the protective fabric, the tape having the bleachable dye thereon secures the protective fabric to ensure that the fabric does not unfold or unwrap to expose the medical instrument. The taped package is then placed in a sterilization chamber to undergo a sterilization process. When the process is complete the wrapped instrument is removed from the chamber and the tape is inspected. The bleachable dye on the tape should have changed color and now acts as a permanent, nonreversible indication that the instrument wrapped within is sterile. The medical instrument remains wrapped within the fabric until ready for use in a medical procedure. At the time of use, the tape is torn, not pealed, and the instrument wrapped therein removed for use. Advantageously, the tape having bleachable dye allows health care providers to differentiate processed from unprocessed items.

Indicator for Limited Re-Use Instrument

A further embodiment of bleachable dye as a chemical indicator in oxidation-type sterilization processes is to configure the dye to change color after a predetermined and specified number of exposures to oxidant sterilization processes where the process is for a known period of time and a known oxidant concentration. In this configuration the bleachable dye is ideally used as a limited re-use indicator for medical instruments having a specified lifetime or designed for a limited number of procedures. To determine when an instrument or device has exceeded its intended number of uses, a surface having bleachable dye thereon is manufactured to change color after being exposed to the oxidation-type sterilant a number of times which the product or device was designed to be used. The surface is then placed on the medical instrument so that each time the medical instrument is used, i.e., for each and every use, the surface is also exposed to the sterilant. Alternatively, the surface may be made as an integral surface of the instrument or an attachable section. Making the surface having bleachable dye an attachable section to the medical instrument provides a different lifetime indicator for an instrument depending upon which bleachable dye surface is attached. For example, an instrument may have a lifetime of 30 uses when new and only 20 uses thereafter between rebuilding. A surface having bleachable dye could be attached accordingly to change color when the appropriate number of uses has been exceeded.

Warranty Indicator

In yet another embodiment, a warranty indicator is provided using the bleachable dye of the present invention. A warranty indicator is an indicator which provides notice when the warranty of a device is still in effect, or, conversely, when the warranty is expired. Advantageously, the warranty indicators of the present invention utilize bleachable dye to provide fast, reliable or undisputable notice when the warranty period is no longer in effect. Furthermore, the warranty indicator of the present invention advantageously provides notice of warranty validity or expiration not based on time period from purchase, but based upon the number of uses of the instrument or device. Warranting a product based on the number of uses instead of the time of purchase eliminates the inequity arising between products that may only be used once a year in comparison to products that are used hundreds of times each year.

The warranty indicator operates using the same principles as the limited re-use indicators described above. However, the dye and surface are configured such that the number of exposures before color change is identical to the number of uses for which the product is warranted.

Other Embodiments

It is further contemplated that non-bleachable dye could be used in conjunction with the bleachable dye to display a color key thereby providing visual color comparison to determine when the bleachable dye has sufficiently changed color and which color indicates an unsterilized state and which color indicates a sterilized state.

It is also contemplated that the bleachable dye may be incorporated with fabric of the type worn by medical professional or of the type described above for use with the chemical indicator tape that will be exposed to a sterilization process using an oxidant. The dye would be impregnated into the fabric to indicate full exposure to a sterilant.

In yet another embodiment, the bleachable dye is incorporated with a count sheet. A count sheet comprises a medium which may be marked upon to record the number and type of medical instruments in the sterilization chamber. A count sheet embodied with bleachable dye thereon would thus record the contents of a sterilization chamber and provide notice that an oxidative-type sterilant entered the chamber. The count sheet could be made up of the type material disclosed herein for other embodiments.

Also within the scope of the invention described herein are other methods and means of exposing the claimed chemical indicators to oxidation-type sterilants. Devices other then the sterilization chamber described herein may be used to provide the sterilizing agents to medical instruments and chemical indicators.

It will be understood that the above described arrangements of apparatus and the methods derived therefrom are merely illustrative of applications of a number of preferred embodiments and it is not intended to limit the scope of the invention to the particular forms set forth, but on the contrary, it is intended to cover such alternatives, modifications and equivalents as may be included within the spirit and scope of the invention as defined by the claims.

What is claimed is:

1. An apparatus for determining exposure to an oxidation-type sterilant or disinfectant, said apparatus comprising:
   a biological indicator for determining the effectiveness of exposure to the oxidation-type sterilant; and
   a chemical indicator for indicating exposure to the oxidation-type sterilant, wherein said chemical indicator comprises:
   a metallic surface; and
   non-pH sensitive indicator means on said surface for indicating exposure to the oxidation-type sterilant.

2. The apparatus of claim 1, wherein said indicator means is an azo dye.

3. The apparatus of claim 1, wherein said indicator means is a permanent indicator means.

4. The apparatus of claim 1, wherein said surface comprises anodized aluminum.

5. The apparatus of claim 1, wherein said surface comprises a chromate conversion coating.

6. The apparatus of claim 1, wherein said biological indicator is a self-contained biological indicator.

7. The apparatus of claim 6, wherein said chemical indicator comprises a generally flat disk on said self-contained biological indicator.

8. The apparatus of claim 1, further comprising a test pack, wherein said test pack is configured to provide for gas flow into said test pack by diffusion and wherein said chemical indicator and said biological indicator are inside said test pack.

9. The apparatus of claim 1, wherein said apparatus comprises a container having a cover, wherein said cover is secured to said container with a tamper-evident device and wherein said tamper-evident device has said surface with said non-pH sensitive bleachable dye thereon.

10. The apparatus of claim 1, wherein said metallic surface comprises a flexible medium having said indicator means on at least a first surface of said flexible medium.

11. The apparatus of claim 10, further comprising adhesive on a second surface of said flexible medium.

12. The apparatus of claim 1, further comprising a warranty indicator which provides notice when a warranty of said apparatus is still in effect.

13. The apparatus of claim 1, wherein said oxidation-type sterilant comprises hydrogen peroxide.

14. The apparatus of claim 13, wherein said oxidation-type sterilant comprises aqueous hydrogen peroxide.

15. The apparatus of claim 13, wherein said oxidation-type sterilant comprises hydrogen peroxide vapor or gas.

16. An apparatus for determining exposure to an oxidation-type sterilant or disinfectant, said apparatus comprising:
   a biological indicator for determining the effectiveness of exposure to the oxidation-type sterilant; and
   a chemical indicator for indicating exposure to the oxidation-type sterilant, wherein said chemical indicator comprises:
   a metallic surface; and
   non-pH sensitive indicator means permanently bound on said surface for indicating exposure to the oxidation-type sterilant.

17. An apparatus for determining exposure to an oxidation-type sterilant or disinfectant, said apparatus comprising:
   a biological indicator for determining the effectiveness of exposure to the oxidation-type sterilant; and
   a chemical indicator for indicating exposure to the oxidation-type sterilant, wherein said chemical indicator comprises:
   a metallic surface; and
   non-pH sensitive indicator means on said metallic surface for indicating exposure to the oxidation-type sterilant,
   wherein at least a portion of said metallic surface is on the outside of a container within which said biological indicator is housed.

* * * * *